United States Patent [19]
Fernandez

[11] 3,932,490
[45] Jan. 13, 1976

[54] DOXYCYCLINE ACETURATE

[76] Inventor: Piedad Amezua Fernandez, Avenida del Poblado s/n - Edificio Montefresno escalera A, 1° derecha, Puerta Hierro, Madrid, Spain

[22] Filed: Dec. 4, 1972

[21] Appl. No.: 312,035

[30] Foreign Application Priority Data
Dec. 4, 1971  Spain .................................. 397675

[52] U.S. Cl. ....... 260/501.11; 260/559 AT; 424/227
[51] Int. Cl.² ..................................... C07C 103/19
[58] Field of Search ................. 260/559 AT, 501.11

[56] References Cited
OTHER PUBLICATIONS
Merck Index, Eight Edition, 1968, pp. 10 and 398 relied on.

Chemical Abstracts, Vol. 67, 1967, 93974s, relied on.

*Primary Examiner*—R. Gallagher
*Assistant Examiner*—Anne Marie T. Tighe
*Attorney, Agent, or Firm*—Woodhams, Blanchard and Flynn

[57] ABSTRACT

Doxycycline aceturate is prepared by reacting doxycycline with aceturic acid in a solvent. The compound is useful for the same pharmacological purposes as doxycycline and is more soluble in water or aqueous solvents so that it is more suitable for parenteral administration.

1 Claim, 1 Drawing Figure

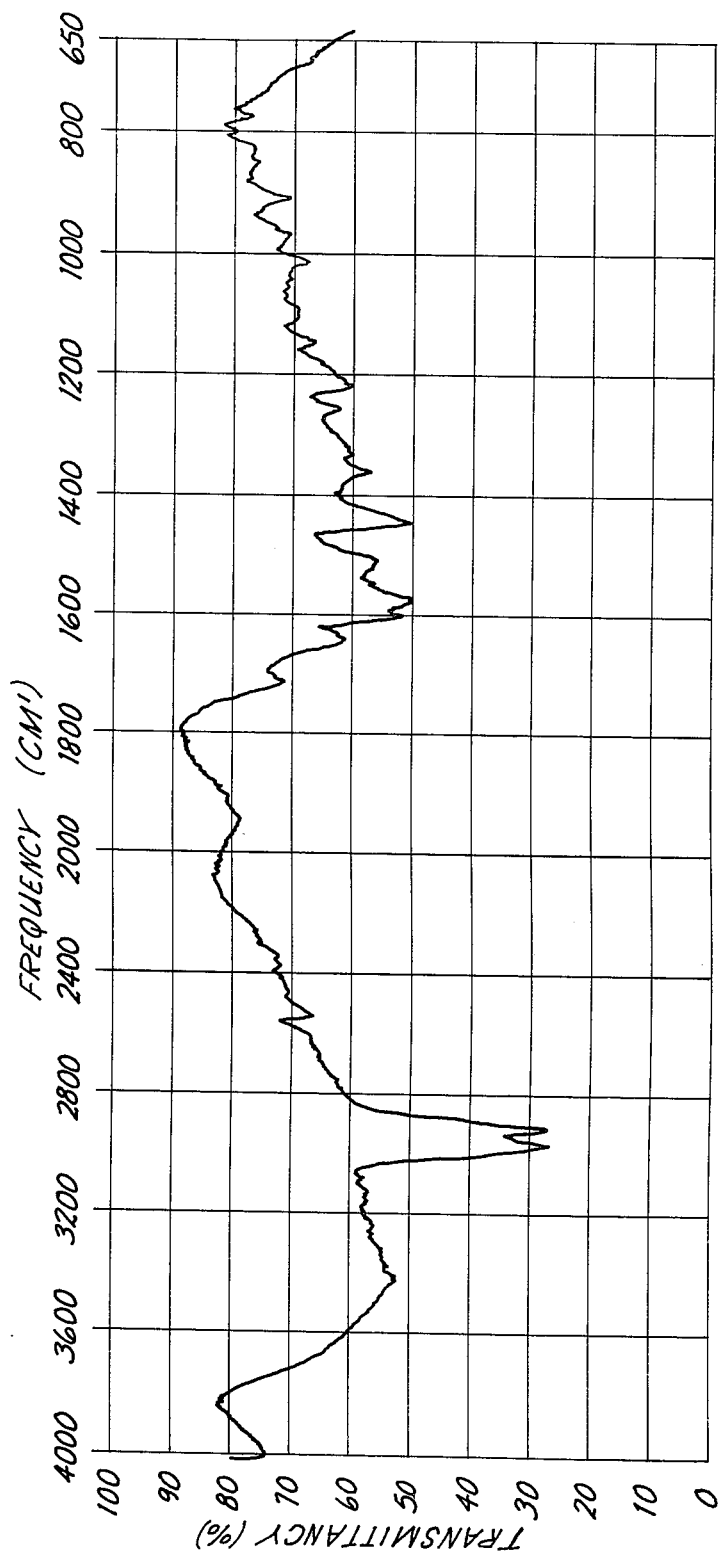

DOXYCYCLINE ACETURATE

BACKGROUND OF THE INVENTION

1. Field of the Invention

This invention relates to doxycycline aceturate and a process for preparing same.

2. Description of the Prior Art

Doxycycline, the most modern broad-spectrum antibiotic of the tetracycline group, surpasses its other congener compounds in therapeutic efficiency because of its higher stability, better gastrointestinal absorbability and its slow urinary elimination. Thus, the concentration of it reaches higher and more stable haematic levels in less time after administration, thus permitting the use of a smaller dosage.

The acute toxicity of this antibiotic is very low (the $DL_{50}$ in mice being over 3984 mg. per kilo) and the chronic toxicity is low also. In extensive tests on mice carried out during periods of up to 180 days with doses thirty times higher than the average daily human therapeutic dose, no histological, anatomical, or physiological alterations were observed in comparison to the control specimens.

The activity of doxycycline, determined "in vitro" in the presence of several Gram-positive and Gram-negative germs, Richettsiae, large viruses, etc., is superior to that of tetracycline, so that its use is specifically indicated in the treatment of bronchopulmonary and urinary tract infections, peritonitis, infected traumatic and post-operatory wounds, burns, etc.

However, the low solubility of doxycycline in water and aqueous solvents is an impediment to its use for parenteral administration, which is sometimes necessary to attain a maximum speed of effect.

SUMMARY OF THE INVENTION

I have discovered doxycycline aceturate, a pharmaceutical compound useful for the treatment of the previously mentioned conditions and which is readily soluble in water or aqueous solvents so that it is well adapted for parenteral administration. This compound can be obtained by reacting doxycycline with aceturic acid (acetylaminoacetic acid). The formula of doxycycline aceturate is:

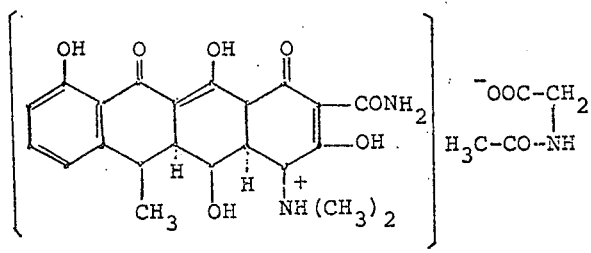

Experiments on laboratory animals have shown that the acute toxicity of the new compound, by oral administration, is very low and is similar to that of doxycycline. The same is true with regard to chronic toxicity. Experiments carried out over periods of more than twenty weeks have shown that the growth rate of the test animals is the same as that of the control animals. There was observed no alterations in glycemia, azotemia, or haematic crasis. On necropsy following the tests, no histological or anatomical alterations were observed.

In absorption tests, in comparison with doxycycline hyclate, no significant differences were observed in the blood plasma concentrations nor in the speed with which such levels were reached with both products.

Doxycycline aceturate is useful for the same pharmacological purposes as doxycycline and can be administered in the dosage forms and amounts conventionally used for doxycycline. In addition, because of its greater solubility in water and aqueous solvents, greater amounts of it can be parenterally administered in a condition suitable for more rapid systemic absorption.

In order to prepare doxycycline acetylaminoacetate, a solution of doxycycline is reacted with a solution of acetylaminoacetic acid, both dissolved in a suitable inert solvent and, if necessary, out of contact with atmospheric humidity. Representative procedures for preparing the compound are described in the following illustrative examples.

EXAMPLE 1

Into an enamel-lined or glass vessel having a capacity of about ten litres, provided with an agitator or stirrer and a thermometer, and which is heated by a hot water bath, a solution of 116 g (0.25 moles) of doxycycline monohydrate is prepared in 8 litres of absolute ethyl alcohol, and same is heated, if necessary, to a temperature of not more than 30° to 35°C. It is advisable to close the feed opening or mouth of the vessel, so as to avoid contact with atmospheric humidity.

The solution of doxycycline can be obtained also, starting from the corresponding hyclate salt, by dissolving 128 g (0.25 moles) of same in a solution which contains 14 g (0.25 moles) of caustic potash in 8 litres of absolute ethyl alcohol, and filtering the precipitated potassium chloride.

Into said doxycycline solution, while stirring same actively, there is poured a solution of 29.3 g (0.25 moles) of acetylaminoacetic acid dissolved in 500 cc of absolute ethyl alcohol, while maintaining the temperature at 30° to 35°C. After the addition of the acid has been completed, 5 g of activated charcoal are added and the agitation is continued for another hour.

The liquid is then flowed under pressure through a filter in order to remove the charcoal, then through a rotary vacuum evaporator to evaporate the alcohol at a pressure of 5 – 10 mm. Hg, and at a temperature of not higher than 30° to 35°C. The separated solid product is finally dried in vacuo over concentrated sulphuric acid. The product is a crystalline powder light yellow in color, and is very soluble in water and lower alcohols. About 140 g of the solid product are obtained, and 60 – 65% of the alcohol employed is recovered for reuse.

EXAMPLE 2

Into an enamel-lined vessel or glass flask having a capacity of about 25 litres, provided with an agitator or stirrer and a thermometer, and which is heated by a hot water bath, there is placed a solution of 2.22 Kg (5 mole) of doxycycline base in 15 litres of dioxane, which dioxane is free of peroxides and which was recently distilled. The solution is heated at 30° to 35°C.

Into said doxycycline solution, there is poured another solution of 585 g (5 mole) of acetylaminoacetic acid dissolved in 2720 cc of dioxane, also recently distilled and free of peroxides, and then 4450 cc of distilled water is gradually poured into the vessel. As the addition of water is carried out the doxycycline salt gradually dissolves. At the end, the reaction liquid has a very faint turbidity. It is stirred for another hour with 30 g of activated charcoal, and it is then filtered. The clean and slightly yellowish liquid is lyophilized, either in the total quantity or in the form of doses in different vessels, by freezing it at −20°C and then drying it for two hours at 40°C and at 10 microns pressure, after which the vessels are sealed or the gross product is sterile packed. About 2800 g of a solid product having characteristics similar to those of the product of Example 1 are obtained.

Analyses of the products prepared by Examples 1 and 2 are as follows:

|   | Theory | Found (Example 1) | Found (Example 2) |
|---|---|---|---|
| C | 55.6 | 56.1 | 55.9 |
| H | 5.5 | 5.7 | 5.7 |
| N | 7.5 | 7.1 | 7.2 |
|   |   |   | −139° C(dec) |

The melting point of the compound is 138°C. The solubility of the compound in water is about 130 mg/ml.

The IR Spectrophotometric curve is as per the attached recording chart.

The embodiments of the invention in which an exclusive property or privilege is claimed are defined as follows:

1. Doxycycline aceturate.

\* \* \* \* \*